United States Patent [19]

Taniguchi et al.

[11] Patent Number: 4,515,776
[45] Date of Patent: May 7, 1985

[54] METHOD OF PREPARING GAMMA GLOBULIN SUITABLE FOR INTRAVENOUS ADMINISTRATION

[75] Inventors: Nobuhiro Taniguchi; Tomohiro Endo, both of Tokyo, Japan

[73] Assignee: Fujirebio Kabushiki Kaisha, Tokyo, Japan

[21] Appl. No.: 484,324

[22] Filed: Apr. 12, 1983

[30] Foreign Application Priority Data

Apr. 16, 1982 [JP] Japan .................................. 57-62366

[51] Int. Cl.³ ..................... A61K 39/395; A61K 35/16
[52] U.S. Cl. ....................................... 424/85; 424/101; 260/112 B
[58] Field of Search ............... 424/101, 85; 260/112 B

[56] References Cited

U.S. PATENT DOCUMENTS

| 3,808,189 | 4/1974 | Breuer | 260/112 B |
|---|---|---|---|
| 4,124,576 | 11/1978 | Coval | 260/112 B |
| 4,164,495 | 8/1979 | Hansen | 260/112 B |
| 4,165,370 | 8/1979 | Coval | 424/85 |
| 4,168,303 | 9/1979 | Nishida et al. | 424/85 |
| 4,276,283 | 6/1981 | Eibl et al. | 424/85 |
| 4,296,027 | 10/1981 | Condie | 260/112 B |
| 4,371,520 | 2/1983 | Uemura et al. | 260/112 B |
| 4,374,763 | 2/1983 | Takagi | 260/112 B |
| 4,379,086 | 4/1983 | Kimura et al. | 260/112 B |

OTHER PUBLICATIONS

Cohn, "Preparation and Properties of Serum and Plasma Proteins. IV. A System for the Separation into Fractions of the Protein and Lipoprotein Components of Biological Tissues and Fluids", Mar. 1946, pp. 459–475.

Oncley, "The Separation of the Antibodies, Isoagglutinins, Prothrombin, Plasminogen and β-Lipoprotein into Subfractions of Human Plasma", Feb. 1949, pp. 541–550.

Primary Examiner—Sam Rosen
Attorney, Agent, or Firm—Flynn, Thiel, Boutell & Tanis

[57] ABSTRACT

A method of preparing gamma globulin suitable for intravenous administration comprising a step of treating a gamma globulin composition containing aggregates of gamma globulin with polypropylene glycol (PPG) and dispersing agents for PPG under selected conditions.

9 Claims, No Drawings

METHOD OF PREPARING GAMMA GLOBULIN SUITABLE FOR INTRAVENOUS ADMINISTRATION

The present invention relates to a method of preparing gamma(γ)globulin suitable for intravenous administration. More particularly, the present invention relates to a method of preparing a gamma globulin composition not containing aggregates of gamma globulin.

BACKGROUND OF THE INVENTION

Gamma globulin is widely used as a therapeutic agent, and generally, it is administrated by intramuscular injection. Impurities, such as aggregates of gamma globulin occasionally contained in gamma globulin products, render hazardous the administration of such gamma globulin products by intravenous injection.

Accordingly, for the purpose of preparing gamma globulin composition free of aggregates thereof, there have been proposed methods of preparing gamma globulin under such conditions that aggregates are not produced. There have also been proposed methods of removing any aggregates that are produced in the course of preparing the gamma globulin, which removal takes place at the last step of the procedure. Such methods for the production or purification of gamma globulin have been disclosed in the literature, for instance, U.S. Pat. Nos. 3,415,804, 3,763,135, 4,093,606 and 4,124,576, and British Pat. No. 1 372 953.

In the methods disclosed in these patents, polyethylene glycol is used for the purpose of production or purification of gamma globulin.

It is an object of this invention to provide a method of preparing gamma globulin, not containing aggregates of gamma globulin, by using polypropylene glycol(PPG).

The inventors have found that gamma globulin products not containing aggregates of gamma globulin can be obtained by treating a gamma globulin composition with PPG under selected conditions as described in the following. In the invention process, the gamma globulin aggregates can be removed, and gamma globulin products suitable for intravenous administration can be obtained from a crude gamma globulin composition, which products do not contain gamma globulin aggregates and have a low anti-complementary activity (ACA). This invention is based on this discovery.

SUMMARY OF THE INVENTION

The method of separating gamma globulin from human blood plasma by fractional precipitation with ethanol is known as the Cohn procedure, described in J. Amer. Chem. Soc. 68, 459–75 (1946) and J. Amer. Chem. Soc. 71, 541–50 (1949).

In the present invention, as a starting material, Cohn Fraction II or Cohn Fraction III were used. Said Cohn Fraction II and Cohn Fraction III are gamma globulin obtained by the so-called Cohn Method 9, as described in J. Amer. Chem. Soc. 71, 546 (1949).

In the method of the present invention, polypropylene glycol (PPG) having a molecular weight of more than 4000 was used. PPG having a molecular weight of 2000 to 10000 also can be used. PPG was used at a concentration of 0.1% to 15% according to pH of solution. (Percentages are by weight/volume.)

As dispersing agents for PPG, monosaccharides such as glucose, galactose, mannose and fructose, amino acids such as glycine and α-alanine, and inorganic salts such as NaCl and KCl, are used. Such dispersing agents are used in a concentration of 0.1% to 1.0%.

The present invention will be illustrated in the following:

A gamma globulin composition containing aggregates of gamma globulin is dissolved in a buffer solution having a pH of 4.0 to 8.0, such as a phosphate buffer solution or an acetate buffer solution, containing dispersing agents. The solution is filtered by asbestos filter, and to the filtrate is added PPG to obtain a dispersion liquid. After the dispersion liquid is stirred for about 30 minutes, it is filtered by asbestos filter. The filtrate is freeze-dried to obtain gamma globulin product in powder form, not containing gamma globulin aggregates and having a low ACA value.

EXAMPLES

The following examples will illustrate this invention. The examples are for illustrative purposes only and do not limit the scope of the invention. The percentages are by weight/volume.

EXAMPLE 1

3.5 g of Cohn Fraction II powder (which was obtained by freeze-drying Cohn Fraction II paste) was dissolved in 40 ml of a 83 mM phosphate buffer solution (pH 7.0) containing glucose in a concentration of 3% and NaCl in a concentration of 0.9%. The solution was filtered by asbestos filter, and to the filtrate was added 1.15 g of PPG (M.W. 4000) to obtain a dispersion liquid containing PPG in a concentration of 3.0%. After the dispersion liquid was stirred for about 30 minutes, it was filtered by asbestos filter to obtain 35 ml of a filtrate having a protein concentration of 5.0%. Yield: 83.3%.

The filtrate was freeze-dried to obtain gamma globulin product in powder form. The ACA value of this product was 8.1 U.

The ACA value was determined by the procedure described in "Experimental Immunochemistry (ed. by Kabat, E. A. & Mayer, M. M.), 2nd Ed. pp 133–240 (1961)".

The ACA value of Cohn Fraction II powder (starting material in this example) was more than 100 U.

EXAMPLE 2

The same procedure as that of Example 1 was repeated except that 20 g of Cohn Fraction II powder, 220 ml of a 83 mM phosphate buffer solution containing glucose (2.25%) and NaCl (0.9%), and 1.9 g of PPG (4000) were used instead of 3.5 g of Cohn Fraction II powder, 40 ml of phosphate buffer solution and 1.15 g of PPG. 296 ml of a filtrate having a protein concentration of 5.0% was obtained in the yield of 85.6%. The ACA value of gamma globulin product was 11.5 U.

EXAMPLE 3

The same procedure as that of Example 1 was repeated except that 50 g of Cohn Fraction II powder, 1600 ml of a 83 mM phosphate buffer solution containing NaCl (0.9%) and glycine (2.5%), and 64 g of PPG (4000) were used. A filtrate having a protein concentration of 5.5% was obtained in the yield of 88.7%. The ACA value of gamma globulin product was 9.7 U.

EXAMPLE 4

The same procedure as that of Example 1 was repeated except that 18 g of Cohn Fraction II powder, 200 ml of a 83 mM phosphate buffer solution containing NaCl (0.9%) and galactose (2.5%), and 8 g of PPG (4000) were used. A filtrate having a protein concentration of 7.3% was obtained in the yield of 86.0%. The ACA value was 12.5 U.

EXAMPLE 5

The same procedure as that of Example 1 was repeated except that 33 g of Cohn Fraction II paste, 55 ml of a 83 mM phosphate buffer solution containing NaCl (0.9%) and α-alanine (2.5%), and 3.4 g of PPG (4000) were used. A filtrate having a protein concentration of 6.7% was obtained in the yield of 90.6%. The ACA value of gamma globulin product was 10.5 U.

EXAMPLE 6

100 g of Cohn Fraction III paste was dissolved in 800 ml of a 10 mM acetate buffer solution, and the solution was centrifuged and then filtered. To the filtrate was added 1.3 g of $AlCl_3$ to adjust to pH 4.6, and the solution was centrifuged and then filtered. The filtrate was dialyzed for two days against 10 mM acetate buffer solution (pH 4.6), and then centrifuged. The resulting supernatant was adjusted to pH 7.0 and concentrated by ultrafiltration. The concentrated solution was filtered by asbestos filter and to the filtrate were added 20 g of glucose (2.25%) and 8 g of NaCl (0.9%) and then 36 g of PPG (4000) to PPG concentration of 4%. The mixture was stirred for about 30 minutes and then filtered by asbestos filter. A filtrate having a protein concentration of 5.0% was obtained. The ACA value of gamma globulin product was zero U.

EXAMPLES 7-13

The gamma globulin products were obtained by repeating the same procedure as that of Example 1 except that Cohn Fraction II powder was treated under the different conditions of PPG concentration and pH as shown in the following.

The ACA values of the products are shown below:

| PPG (%) | pH  | ACA (U) |
|---------|-----|---------|
| 0.85    | 7.0 | 2.1     |
| 1.0     | 7.0 | 10.8    |
| 2.0     | 7.0 | 12.5    |
| 4.0     | 4.0 | 15.2    |
| 4.0     | 5.0 | 1.3     |
| 4.0     | 6.0 | 6.9     |
| 4.0     | 8.0 | 14.3    |

Gamma globulin products having the ACA value of lower than 20 U can be used for intravenous administration. Therefore, gamma globulin prepared by the method of this invention is suitable for intravenous administration.

We claim:

1. A method of preparing gamma globulin suitable for intravenous administration, which comprises the steps of:
    dissolving (a) a gamma globulin composition selected from the group consisting of Cohn Fraction II and Cohn Fraction III, said composition containing aggregates of gamma globulin, in (b) a buffer solution having a pH in the range of 4.0 to 8.0, to obtain a solution;
    adding to said solution (1) at least 0.1 to 15% of polypropylene glycol having a molecular weight in the range of 2000 to 10,000 and (2) a dispersing agent in an amount effective to disperse said polypropylene glycol in said solution, said dispersing agent being selected from the group consisting of monosaccharides, amino acids, inorganic salts, and mixtures thereof, thereby to obtain a dispersion liquid;
    and filtering said dispersion liquid to obtain a filtrate containing said gamma globulin suitable for intravenous administration.

2. A method according to claim 1, wherein said buffer solution is a phosphate buffer solution or an acetate buffer solution.

3. A method according to claim 1, wherein said polypropylene glycol has a molecular weight of 4000.

4. A method according to claim 1, wherein said dispersing agent is selected from the group consisting of glucose, galactose, mannose, fructose, glycine, α-alanine, NaCl and KCl.

5. A method according to claim 1, wherein said dispersing agent is used in a concentration of 0.1%-1.0%.

6. A method of preparing gamma globulin suitable for intravenous administration, which comprises the steps of:
    dissolving (a) a gamma globulin composition selected from the group consisting of Cohn Fraction II and Cohn Fraction III obtained by Cohn Method 9, and containing aggregates of gamma globulin, in (b) a phosphate buffer solution or an acetate buffer solution having a pH in the range of 4.0 to 8.0, said buffer solution containing 0.1% to 1.0% of a dispersing agent for polypropylene glycol selected from the group consisting of monosaccharides, amino acids, inorganic acids, and mixtures thereof, to thereby obtain a solution;
    then filtering said solution to obtain a first filtrate containing dissolved gamma globulin;
    then adding to and mixing in said first filtrate from 0.1 to 15% of polypropylene glycol having molecular weight in the range of 2000 to 10,000 to thereby obtain a dispersion liquid; and
    then filtering said dispersion liquid to obtain a second filtrate containing said gamma globulin suitable for intravenous administration.

7. A method according to claim 6, further comprising a step of freeze drying said second filtrate to obtain a gamma globulin powder.

8. A method according to claim 6, wherein said dispersing agent is at least one member selected from the group consisting of glucose, galactose, mannose, fructose, glycine, α-alanine, NaCl and KCl.

9. A method according to claim 6, wherein said steps of filtering said solution and filtering said dispersion liquid are conducted using an asbestos filter.

* * * * *

UNITED STATES PATENT AND TRADEMARK OFFICE
CERTIFICATE OF CORRECTION

PATENT NO. : 4 515 776

DATED : May 7, 1985

INVENTOR(S) : Nobuhiro TANIGUCHI et al

It is certified that error appears in the above-identified patent and that said Letters Patent is hereby corrected as shown below:

Column 4, line 39; change "inorganic acids" to ---inorganic salts---.

Signed and Sealed this

Twenty-fourth Day of December 1985

[SEAL]

Attest:

DONALD J. QUIGG

Attesting Officer

Commissioner of Patents and Trademarks